(12) United States Patent
Robinson et al.

(10) Patent No.: US 11,944,718 B1
(45) Date of Patent: Apr. 2, 2024

(54) COMPOSITIONS AND MANUFACTURE OF ALLOGRAFT TISSUE

(71) Applicant: Healthtech Solutions, Inc., Tuckahoe, NY (US)

(72) Inventors: Bradley Robinson, North Salt Lake, UT (US); Douglas Ivins Schmid, Sandy, UT (US); Thayne Sherman Ekness, Denver, CO (US)

(73) Assignee: Healthtech Solutions, Inc., Tuckahoe, NY (US)

( * ) Notice: Subject to any disclaimer, the term of this patent is extended or adjusted under 35 U.S.C. 154(b) by 0 days.

(21) Appl. No.: 18/083,019

(22) Filed: Dec. 16, 2022

Related U.S. Application Data

(60) Provisional application No. 63/357,125, filed on Jun. 30, 2022, provisional application No. 63/340,683, filed on May 11, 2022.

(51) Int. Cl.
| | |
|---|---|
| *A61L 27/36* | (2006.01) |
| *A01N 1/02* | (2006.01) |
| *A61K 35/50* | (2015.01) |
| *A61L 27/22* | (2006.01) |
| *A61L 27/60* | (2006.01) |

(52) U.S. Cl.
CPC ........ *A61L 27/3604* (2013.01); *A01N 1/0284* (2013.01); *A01N 1/0289* (2013.01); *A61K 35/50* (2013.01); *A61L 27/227* (2013.01); *A61L 27/60* (2013.01)

(58) Field of Classification Search
None
See application file for complete search history.

(56) References Cited

U.S. PATENT DOCUMENTS

| | | | | |
|---|---|---|---|---|
| 8,323,701 B2 * | 12/2012 | Daniel | ............ | A61K 35/33 |
| | | | | 623/23.72 |
| 8,709,494 B2 * | 4/2014 | Daniel | ............ | A61L 27/54 |
| 9,186,382 B2 | 11/2015 | Daniel | | |
| 9,265,801 B2 | 2/2016 | Daniel | | |
| 10,688,220 B2 | 6/2020 | Hopkinson | | |
| 11,154,641 B2 | 10/2021 | Daniel | | |
| 11,166,800 B2 | 11/2021 | Deister | | |
| 11,413,372 B2 | 8/2022 | Daniel | | |
| 2008/0193554 A1 * | 8/2008 | Dua | ............ | A61P 43/00 |
| | | | | 435/1.3 |
| 2013/0136773 A1 | 5/2013 | Horton | | |
| 2018/0280572 A1 * | 10/2018 | Daniel | ............ | A61P 17/02 |
| 2018/0361026 A1 | 12/2018 | Qin | | |
| 2019/0290802 A1 | 9/2019 | Goldstein | | |
| 2021/0069257 A1 | 3/2021 | Olson | | |

OTHER PUBLICATIONS

Zhao et al, Outcomes of different-method-preserved amniotic membrane graft after transplanted to rabbit occular surface, Jounal of Third Military Medical Univ., 2003, Abstract.
Offer of Sale, Aug. 2021.

* cited by examiner

*Primary Examiner* — Allison M Fox
(74) *Attorney, Agent, or Firm* — Greenberg Traurig, LLP

(57) ABSTRACT

The disclosure herein relates to isolated and purified mammalian fetal allografts and kits and compositions containing these. Also disclosed are methods of preparing isolated and purified mammalian fetal allografts; methods of contacting a wound of a subject with these, and methods of treating a disease or condition with these.

30 Claims, 1 Drawing Sheet

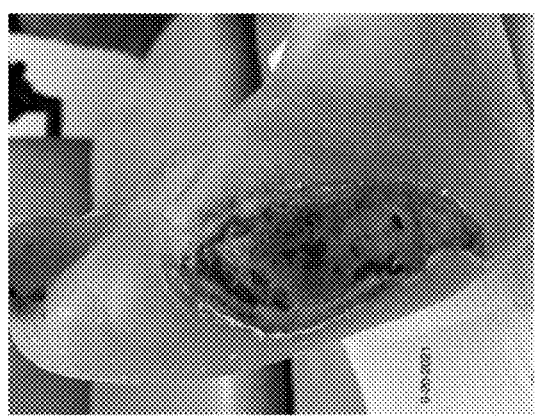
6 months after application
4 weeks after application
2 weeks after application
Before AmnioBind

COMPOSITIONS AND MANUFACTURE OF ALLOGRAFT TISSUE

CROSS REFERENCE TO RELATED APPLICATIONS

This application claims priority to U.S. provisional application No. 63/340,683, filed May 11, 2022 and U.S. provisional application No. 63/357,125, filed Jun. 30, 2022, both of which are incorporated herein by reference in their entirety.

SUMMARY

Certain aspects of the disclosure herein pertain to an isolated and purified mammalian, for example human, fetal allograft, comprising: an amnion layer and a chorion layer and an intermediate layer positioned between the amnion layer and the chorion layer; wherein the amnion layer and the chorion layer and the intermediate layer are substantially unseparated or are unseparated, and:
1) a thickness of the intermediate layer of the isolated and purified mammalian, for example human, fetal allograft ranges from 661 micrometers to about 2000 micrometers as measured by a micrometer;
2) the isolated and purified mammalian, for example human, fetal allograft has an average thickness that ranges from about 961 micrometers to about 2350 micrometers; or
3) a combination of 1) and 2);
and optionally the isolated and purified mammalian, for example human, fetal allograft further comprises an exogenous amount of: glutamine, a salt thereof, arginine, a salt thereof, or any combination thereof, in an amount ranging from about 1 ng to about 1000 micrograms, for example, about 10 ng, about 50 ng, about 100 ng, about 200 ng, about 300 ng, about 400 ng, about 500 ng, about 1 microgram, about 10 micrograms, about 50 micrograms, about 100 micrograms, about 500 micrograms, or about 750 micrograms.

Regarding the composition of the isolated mammalian, for example human, fetal allograft, in some cases, the amnion may comprise the amnion layer, the intermediate layer, and the chorion layer in an unseparated state.

Still further, in certain cases, the isolated and purified mammalian, for example human, fetal allograft is sterile. Additionally, in certain cases the isolated and purified mammalian, for example human, fetal allograft is dehydrated or hydrated. In the case of dehydration, the isolated and purified mammalian, for example human, allograft may be dehydrated via vacuum dehydration.

In certain cases, the isolated and purified mammalian, for example human, fetal allograft may have an average thickness that ranges from about 961 micrometers to about 2350 micrometers.

The isolated and purified mammalian, for example human, fetal allograft, in certain cases, may not comprise maternal decidua cells. In other instances, the isolated and purified mammalian, for example human, fetal allograft may substantially not comprise cells. Likewise, in certain instances, the isolated and purified mammalian, for example human, fetal allograft, may not comprise or substantially comprise a blood clot, a blood component, an epithelial cell, a fibroblast, a trophoblast, a blood cell, or any combination thereof. In certain instances, the allograft does not substantially comprise hemoglobin. Another property of the isolated and purified mammalian, for example human, fetal allograft may include a substantial lack, or a lack, of translucence. The substantial lack, of the lack, of translucence may be determined by visual inspection that comprises holding the isolated and purified mammalian, for example human, fetal allograft between a visible light source and a surface having marking(s) and visually detecting whether the marking(s) on the surface are visible through the isolated and purified mammalian, for example human, fetal allograft.

The isolated and purified mammalian, for example human, fetal allografts of the present disclosure may, in some instances, not be compressed, folded, or compressed and folded.

In certain instances, the isolated and purified mammalian, for example human, fetal allograft may comprise at least one of: a human epidermal growth factor, Syndecan-1, MMP-9 (matrix metalloproteinase-9), TIMP-1 (Tissue Inhibitor of metalloproteinase-1), LAP (surrogate for transforming growth factor-beta1, TGF-beta1), Cystatin C, Galectin-3, BMP-2 (Bone Morphogenic Protein-2), M-CSF (macrophage colony stimulating factor 1), sICAM-1 (soluble intracellular adhesion molecule-1), and IL-37 (Interleukin-37), or any combination thereof.

Still further, the isolated and purified mammalian, for example human, fetal allograft in some instances may comprise a marking. In certain instances, the isolated and purified mammalian, for example human, fetal allograft comprises one or more pre-made attachment points. Regarding the pre-made attachment points, such points may comprise one or more etchings, and wherein the one or more etchings are configured to: a) increase visibility of the one or more pre-made attachment points; b) guide placement of the isolated and purified human fetal allograft onto recipient tissues; determine an orientation of the isolated and purified mammalian, for example human, fetal allograft; c) assist with placement of one or more nerve ends at a measured distance within the isolated and purified mammalian, for example human, fetal allograft; or any combination thereof.

In certain instances, the isolated and purified mammalian, for example human, fetal allograft may not substantially comprise, or may not comprise, hemoglobin. Alternatively, the isolated and purified mammalian, for example human, fetal allograft may comprise hemoglobin in an amount ranging from: about micrograms to about 50 micrograms; about 0.01 micrograms to about 50 micrograms; about 0.1 micrograms to about 50 micrograms; about 1 microgram to about 50 micrograms; about 1 microgram to about 40 micrograms; about 1 microgram to about 30 micrograms; about 1 microgram to about 20 micrograms; about 1 microgram to about 10 micrograms; about 14 micrograms to about 50 micrograms; about 15 micrograms to about 50 micrograms; about 20 micrograms to about 50 micrograms; about 25 micrograms to about 50 micrograms; about 30 micrograms to about 50 micrograms; about 35 micrograms to about 50 micrograms; about 40 micrograms to about 50 micrograms; about 45 micrograms to about 50 micrograms; about 1 ng to about 60 ng; about 1 ng to about 50 ng; about 1 ng to about 40 ng; about 1 ng to about 30 ng; about 1 ng to about 20 ng; about 1 ng to about 10 ng; about 1 ng to about 50 ng; about 1 ng to about 40 ng; about 1 ng to about 30 ng; about 1 ng to about 20 ng; about 1 ng to about 15 ng; about 1 ng to about 10 ng; about 1 ng to about 5 ng; or less than or equal to about: 60 ng, 50 ng, ng, 30 ng, 20 ng, 10 ng, or 5 ng; per mg of the isolated and purified mammalian, for example human, fetal allograft, or per mg of the dry or dehydrated isolated and purified mammalian, for example human, fetal allograft. The amount of hemoglobin present can be measured by an enzyme linked immunosorbent assay (ELISA).

The isolated and purified mammalian, for example human, fetal allograft in certain instances, may be in the form of a fine powder. The isolated and purified mammalian, for example human, fetal allograft in some instances may be in the form of a square, a circle, an oval, a rectangle, an irregular shaped, or a circle. The isolated and purified mammalian, for example human, fetal allograft may, in some instances, have a regular or an irregular shape, or may be in the form of a sheet, may be a conical shape, or may be in the form of a cylindrical shape. In some instances, the isolated and purified mammalian, for example human, fetal allograft further comprise at least one of an excipient, a diluent, a carrier, a preservative, or any combination thereof, any of which may be pharmaceutically acceptable. Regarding the shape, the isolated and purified mammalian, for example human, fetal allograft, in some instances, may have a height and length independently, of about: 1, 2, 3, 4, 5, 6, 7, 8, 9, 10, 11, 12, 13, 14, 15, 16, 17, 18, 19, or 20 cm.

The isolated and purified mammalian, for example human, fetal allograft may be contained in a kit. Such a kit may include a container with markings on the container. The container may be in the form of an envelope, a pouch, or a shaker; or in some instances, the container can comprise: a glass, a plastic, a metal, or any combination thereof; or any combination of these. The container, in some instances, may contain one or more transparent surfaces. The container may, in some instances, contain a mark on a surface of the container to help a physician or health care provider orient the isolated and purified mammalian, for example human, fetal allograft when, for example, contacting it with or in a wound.

Other aspects disclosed herein pertain to using the isolated and purified mammalian, for example, human fetal allograft. In one embodiment, a method can comprise contacting an effective amount of the isolated and purified mammalian, for example human, fetal allograft with a wound of a subject, which can be a mammal, which can be a human, which can be a mammal or a human in need thereof. In certain cases, the method concerns treating a disease or condition in a subject, which can be a mammal, which can be a human, which can be a mammal or a human in need thereof, the method comprising treating a wound which can comprise an incision, a laceration, an abrasion, an avulsion, a burn, a contusion, a penetrating wound, an ulcer, a diabetic ulcer, a diabetic foot ulcer, and any combination thereof. The treatment of the wound may comprise contacting the wound with the therapeutically effective amount of the isolated and purified mammalian, for example human, fetal allograft.

The method of treatment, in certain instances, may further comprise administering a second therapeutic, and wherein the second therapeutic is administered: consecutively or concurrently; and optionally, wherein the second therapeutic is administered concurrently in a composition comprising the isolated and purified mammalian, for example human, fetal allograft and the second therapeutic.

In certain instances, the second therapeutic may comprise a phosphodiesterase type 5 inhibitor or a pharmaceutically acceptable salt thereof, nitroglycerine, a nitrate, a nitric oxide donor or a pharmaceutically acceptable salt thereof, nitric oxide, an antibiotic or pharmaceutically acceptable a salt thereof, a surgical process, a debridement, or any combination thereof. If the second therapeutic is administered concurrently with the isolated and purified mammalian, for example human, fetal allograft, the second therapeutic can be administered separately from the isolated and purified human fetal allograft, or can be administered in the form of a composition that contains the second therapeutic and the isolated and purified mammalian, for example human, fetal allograft.

The treatment of a disease or condition with the isolated and purified mammalian, for example human, fetal allograft, and optionally a second therapeutic, or the contacting of a wound with the isolated and purified mammalian, for example human, fetal allograft, can result in a decreased healing time when compared to a healing time arising from a comparable method employing an otherwise comparable isolated and purified mammalian, for example human, fetal allograft where in the otherwise comparable isolated and purified mammalian, for example human, fetal allograft:

a) the amnion layer and the chorion layer were separated and subsequently reattached prior to introduction in a subject; or b) the amnion layer and the chorion layer are substantially unseparated or are unseparated, and the otherwise comparable isolated and purified human fetal allograft comprises an intermediate layer having a thickness of about 100 micrometers to about: 660, 650, 640, 630, 620, 610, 600, 590, 580, 570, 560, 550, 540, 530, 520, 510, 500, 490, 480, 470, 460, 450, 425, 400, 375, 350, 325, 300, 275, 250, 225, or 200 micrometers; or c) the amnion layer and the chorion layer are unseparated and the otherwise comparable isolated and purified human fetal allograft has average thickness from about 100 micrometers to less than about 660 micrometers, from about 100 micrometers to less than about 600 micrometers, from about 100 micrometers to less than about 500 micrometers, from about 100 micrometers to about less than 400 micrometers, or from about 100 micrometers to about less than 300 micrometers;

or any combination of these,

Other aspects of the disclosure pertain to a method of making the hydrated or dehydrated (substantially dry) isolated and purified mammalian, for example human, fetal allograft wherein the method comprises:

a) optionally removing a blood component from a precursor isolated and purified mammalian, for example human, fetal allograft;

b) optionally removing a blood clot from a precursor isolated and purified mammalian, for example human, fetal allograft;

c) optionally removing a tissue section from a precursor isolated and purified mammalian, for example human, fetal allograft; and d) soaking a precursor isolated and purified mammalian, for example human, fetal allograft in an aqueous salt solution for a time period of at least about: 2 days, 3 days, 4 days, 5 days, 6 days, 7 days, 8 days, 9 days, 10 days, 11 days, 12 days, 13 days, 14 days; or for a time period ranging from about 2 days to about 14 days; or for a time period ranging from 3.5, about 3.5, 4.125 days, about 4.125 days, 4.5 days, about 4.5, 5, or about 5 days to about 7 days, or about 3.5 days to about 7 days, wherein a day is 24 hours; thereby forming a soaked precursor isolated and purified mammalian, for example human, fetal allograft. The soaking may be done using one salt solution—for example, soaking in a same salt solution, for example, for about seven days. Alternatively, the soaking can be done by using different, for example, 2 or 3 or 4 or 5 or 6 or 7 or 8 or 9 or 10 or more or salt solutions, which may independently be the same or different in terms of salt contained therein, concentration of a salt contained, therein or both, for a total time—for example, for a total time of 7 days. Soaking in the salt solution can provided a salt soaked precursor isolated and purified mammalian, for example human, fetal allograft.

Still further, in the case of soaking in the aqueous salt solution, the soaking may be for a period of about 7 or about 8 days. In certain instances, the soaking includes a salt which can be a sodium salt, a potassium salt, a lithium salt, a calcium salt, a magnesium salt, a manganese salt, a copper salt, a zinc salt, an organic salt, an inorganic salt, a chloride salt, a sulfate salt, a carbonate salt, a phosphate salt, an iodide salt, a bromide salt, an acetate salt, or any combination thereof. In some instances, the salt can be sodium chloride, potassium chloride, lithium chloride, calcium chloride, magnesium chloride, manganese chloride, copper chloride, zinc chloride, sodium sulfate, potassium sulfate, lithium sulfate, calcium sulfate, magnesium sulfate, manganese sulfate, copper sulfate, zinc sulfate, sodium carbonate, potassium carbonate, calcium carbonate, magnesium carbonate, manganese carbonate, copper carbonate, zinc carbonate, sodium phosphate, potassium phosphate, lithium phosphate, calcium phosphate, magnesium phosphate, manganese phosphate, copper phosphate, zinc phosphate, sodium acetate, potassium acetate, lithium acetate, calcium acetate, magnesium acetate, manganese acetate, copper acetate, zinc acetate, or any combination thereof. The concentration of the salt in the aqueous salt solution may range solution range from about 0.01 M to about 4.0 M; or about 0.1 M, or about 1.0 M, or about 1.5 M, or about 2.0 M, or about 2.5 M, or about 3.0 M, or about 3.5 M; or about 0.6 g salt per 100 mL of water; or about 0.7 g of salt per 100 mL of water; or about 0.8 g of salt per 100 mL of water; or about 0.9 g of salt per 100 mL of water; or about 1.0 g of salt per 100 mL; or about 1.1 g of salt per 100 mL; or about 1.2 g of salt per 100 mL; or about 1.3 g of salt per 100 mL; or about 1.4 g or salt per 100 ml of water; or about 1.5 g of salt per 100 mL of water; or about 1.6 g of salt per 100 mL of water; or from about 0.6 g of salt per 100 mL of water to about 1.6 g of salt per 100 mL of water. The solutions can, optionally, contain one or more further ingredients.

Still further, in certain cases, after soaking in a salt solution, the salt soaked precursor isolated and purified mammalian, for example human, fetal allograft may be subjected to an aqueous rinse, which can be a soak, thereby forming a hydrated (wet) isolated and purified mammalian, for example, human fetal allograft. The aqueous rinse or soak may be conducted, for example, employing a deionized water, a distilled water, a reverse osmosis purified water, a purified water, tap water, or any combination thereof. Still further the aqueous rinse or soak may range from about 16 hours to about 72 hours, or about: 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 54, 55, 56, 57, 58, 59, 60, 61, 62, 63, 64, 66, 67, 68, 69, 70, 71, or 72 hours.

After rinsing, the isolated and purified mammalian, for example human, fetal allograft is hydrated and may be further dried or dehydrated, thereby forming a dehydrated (substantially dry) isolated and purified mammalian, for example, human, fetal allograft. In certain instances, the drying may comprise vacuum drying or dehydrating. The vacuum drying or dehydrating can occur with or without the addition of heat. In some instances, the drying or dehydrating does not employ lyophilizing. In some instances, the drying or dehydrating employs lyophilizing.

In certain cases, the hydrated or the dehydrated isolated and purified mammalian, for example human, fetal allograft may be shaped. The shaping may comprise cutting or slicing or tearing or ripping or rending or pulling apart or molding or any combination thereof.

In certain instances, the methods described herein may include packing the now isolated and purified mammalian, for example human, fetal allograft, which can be hydrated or dehydrated, into a container.

In certain aspects of the methods, the methods herein my including contacting or not contacting with one or more of the following substances: N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, a polyoxyethylene sorbitol ester, or any combination thereof is omitted. Likewise, the step of any substantial contact with N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, a polyoxyethylene sorbitol ester, or any combination thereof.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF DESCRIPTION OF THE DRAWINGS

FIG. 1 shows a wound before and at specified time points after contacting with an isolated and purified human fetal allograft.

DETAILED DESCRIPTION

Definitions

As used herein, the singular forms "a", "an", and "the" include plural references unless the context clearly dictates otherwise. Any reference to "or" herein may be intended to encompass "and/or" unless otherwise stated.

As used herein, in some instances, an "M" when placed after a number can mean molar. For example, 10 M can mean 10 Molar, which is the number of moles of a substance per liter (L) of a solution.

As used herein, in some instances, "mL" can mean milliliters, for example, 10 mL can be 10 milliliters.

An amino acid or salt thereof herein can be of plant origin or of animal origin, or both.

As used herein, and unless indicated otherwise, average and mean are used interchangeably. For example, average thickness is interchangeable with mean thickness.

As used herein, "substantially" can mean, for example, in the context of the layers of an allograft herein being substantially unseparated, that the layers are about: 90%, 91%, 92%, 93%, 94%, 95%, 96%, 97%, 98%, or 99% unseparated as measured by visual inspection. When substantially modifies a term such as substantially not translucent, the amount of translucence can be about: 1%, 2%, 3%, 4%, 5%, 6%, 7%, 8%, 9%, or 10%. In some embodiments, substantially without a cell or cells can mean has less than or equal to about: 100, 50, 25, 10, 5, or 1 cell(s).

Thickness as described herein can be measured, for example, by a microscope or a micrometer. Length and height can be measured, for example, by a ruler or a micrometer.

As used herein, the term "about" may mean the referenced numeric indication plus or minus: 5%, 10%, 15%, or 20% of that referenced numeric indication. In some instances, "about" may mean the referenced numeric indication plus or minus 15% of that referenced numeric indication. In some instances, "about" may mean the referenced numeric indication plus or minus 20% of that referenced numeric indication.

The phrase "pharmaceutically acceptable" may be employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" as used herein may refer to a pharmaceutically acceptable material, composition or vehicle, such as a liquid or solid filler, diluent, excipient, carrier, solvent or encapsulating material.

The terms "treat," "treating" or "treatment," as used herein, may include at least partially: alleviating, abating or ameliorating a disease or condition symptom; preventing an additional symptom; ameliorating or preventing the underlying causes of symptom; inhibiting the disease or condition, e.g., at least partially arresting the development of the disease or condition; relieving the disease or condition; causing regression of the disease or condition (e.g. causing a wound to regress); relieving a condition caused by the disease or condition; or stopping a symptom of the disease or condition either prophylactically, therapeutically or both. Treatment may include treatment of a wound, regrowth of tissue, reducing a wound, reducing scarring, regrowth of tissue from an ulcer, regrowth of tissue from a burn, structural strengthening of a tissue, preventing a wound, preventing scarring, gain of motor function, decreasing or preventing an infection, decreasing or preventing an inflammation, decreasing or preventing pain, decreasing or preventing an immune response, decreasing or preventing the risk of cancer, increasing beneficial tissue growth, or some combination thereof in an otherwise substantially identical subject who has not been treated.

As used herein, a "pharmaceutical agent" may refer to an agent or a therapy that may be used to prevent, diagnose, treat, or cure a disease, or combinations thereof. In some cases, a pharmaceutical agent can comprise a purified human allograft, an amnion layer, a chorion layer, an intermediate layer, a derivative of these, or some combination thereof.

In some aspects, a method described herein may comprise administering a therapeutically effective amount of these to a subject, who can be a human or animal subject, who can be a mammal.

Included in the present disclosure may be salts, including pharmaceutically acceptable salts, of the compositions described herein. The compounds or compositions of the present disclosure that may possess a sufficiently acidic, a sufficiently basic, or both functional groups, may react with any of a number of inorganic bases, inorganic acids, or organic acids, to form a salt. Alternatively, compositions containing compounds that are inherently charged, such as those with quaternary nitrogen, may form a salt with an appropriate counterion, e.g., a halide such as bromide, chloride, fluoride, or iodide.

As used herein, "agent" or "biologically active agent" or therapeutic may refer to a biological, pharmaceutical, or chemical compound or a salt of any of these. structures. In addition, various natural sources may provide compounds for screening, such as plant or animal extracts, and the like.

In some aspects, disclosed herein, compounds may be in a form of pharmaceutically acceptable salts. As well, active metabolites of these compounds having the same type of activity may be included in the scope of the present disclosure. In addition, the compounds described herein may exist in unsolvated as well as solvated forms with pharmaceutically acceptable solvents such as water, ethanol, and the like. The solvated forms of the compounds presented herein may also considered to be disclosed herein.

In some aspect herein, a mammal can include: a human, a pig, a cow, a dog, a cat, a goat, a monkey, an ape, a primate, a horse, a bison, and the like. A mammal can be a mammal in need thereof.

Overview

Disclosed herein are compositions and methods of contacting a wound in a subject, and methods of treatment of a wound in a subject, involving contacting or treating by contacting the wound in a subject with an isolated and purified mammalian, for example human, fetal allograft. Isolated and purified mammalian fetal allografts may be derived from placental tissue which supports the transport of oxygen, nutrients and the like from the mother to the fetus during fetal development. These isolated and purified mammalian fetal allografts may function as treatments for wounds such as skin transplantation grafts, treatment for diabetic associated ulcers, burns, damage from oral surgery, rectal surgery, vaginal surgery, arthroplasty, and the like.

The source material used for the production of isolated and purified mammalian fetal allografts, such as isolated and purified human fetal allografts, may be obtained from a mammalian placenta. For example, an isolated and purified bovine fetal allograft may use or be derived from a placenta from a cow that has just or recently given birth. Likewise, an isolated and purified human fetal allograft may use or be derived from a placenta from a human, for example a human who has just or recently given birth. In general, placental membranes may possess numerous components such as fully differentiated cells, partially differentiated stem cells, extracellular matrix material, cytokines, and regulatory factors such as growth factors. These membranes may possess properties important for tissue regeneration and wound healing. Additionally, they may have low immunogenicity, and may have, for example, anti-fibrosis, anti-scarring, anti-inflammation, and anti-pain properties.

The amnion, intermediate layer, and chorion are composed of numerous components, including cells, growth factors, extracellular matrix molecules, and other biomolecules which can be important for tissue regeneration and wound healing. For example, the amnion, intermediate layer, or chorion may contain cells, such as epithelial cells, fibroblasts, and trophoblasts; growth factors, such as fibroblast growth factors, epidermal growth factor, transforming growth factor (TGF) beta, platelet-derived growth factors, etc.; extracellular matrix molecules such as collagens, elastins, proteoglycans, non-proteoglycan polysaccharides, fibronectins, laminins, nidogens, etc.; and other biomolecules, such as cytokines (e.g., interleukins, TGF-beta, etc.), metalloproteinases, tissue inhibitors of metalloproteinases (TIMPs), etc.

The placental tissue may comprise four layers: an epithelial monolayer, a basement membrane, a compact layer, and a fibroblast layer. The epithelial layer of the placental tissue can be composed of a single layer of epithelial cells arranged on the basement membrane Amniotic epithelial cells may include amniotic stem cells or have stem cell-like characteristics. For example, the cells of the epithelial layer of the placental tissue may be capable of differentiating into or producing, in the presence of a differentiation-inducing factor, at least one different cell lineage, such as osteogenic, adipogenic, chondrogenic, myogenic, neurogenic, epithelial, or other cell lineages. Amniotic stem cells or cells with stem cell-like characteristics may also be found in other layers of the amnion or chorion.

The base of the epithelial cell layer may be in contact with the basement membrane of the amnion. The basement membrane of the amnion may be a thin layer comprising extracellular matrix components, including collagen types III, IV, and V, noncollagenous glycoproteins (e g, laminins, fibronectins, and nidogens), and proteoglycans (e.g., perlecans). The compact layer of the amnion may be a dense, fibrous network comprising extracellular matrix components, including collagens (e.g., collagen types I, III, V, and VI) and fibronectins, and is almost devoid of cells. The fibroblast layer may, in some instances, be the thickest layer of the amnion and comprises fibroblasts and extracellular matrix components, such as collagens (e.g., collagen types I, III, and VI) and noncollagenous glycoproteins (e.g., laminins, fibronectins, and nidogens).

Amniotic epithelial cells may lack HLA-A, HLA-B (Class IA) and HA-DR (Class II) on their surfaces suggesting that these cells may be immunologically inert and have reduced risk of rejection or immune reaction upon transplantation.

The intermediate layer, or spongy layer, may be the interface between the amnion and the chorion. The intermediate layer may comprise extracellular matrix components, such as collagens (e.g., collagen types I, III, and IV), proteoglycans, and glycoproteins. In some instances, "intermediate layer" includes cells or an extracellular matrix derived from an intermediate layer. For example, in some instances, when an amnion and a chorion are separated along an intermediate layer, the cells or extracellular matrix derived from the intermediate layer may remain associated with the fibroblast layer of the amnion or may remain associated with the reticular layer of the chorion.

The chorion may be several times thicker than the amnion and may be composed of three layers: a reticular layer, a basement membrane, and a trophoblast layer. The reticular layer may be in contact with the intermediate layer and comprises extracellular components, such as collagens (e.g., collagen types I, III, IV, V, and VI) and proteoglycans. The basement membrane may be between the reticular layer and trophoblast layer of the chorion. Components of the basement membrane of the chorion may comprise collagens (e.g., collagen type IV), laminins, and fibronectins. The trophoblast layer may comprise several layers of trophoblasts and is in contact with the maternal endometrium. As used herein, the term "trophoblast layer" includes cells, extracellular matrix, or blood vessels that may be present and that are derived from the capsular decidua, the portion of the maternal endometrium facing the uterine cavity.

Surprisingly, the inventors have discovered novel methods of producing isolated and purified mammalian, for example human, fetal allografts using, among other techniques, exposure to aqueous salt solutions, for example aqueous saline solutions, for example by soaking, followed by exposure to water, for example by soaking, which may not contain, or may not substantially contain, detergent(s) and/or salts; and the methods in some instances may not employ freeze drying and in some instances employ vacuum drying. The methods can surprisingly and superiorly result in less, or substantially no damage, or no damage, for example, substantially no separation, or no separation, of allograft layers, during the preparation of these isolated and purified mammalian, for example human, allografts. The methods surprisingly and superiorly can also substantially increase a thickness, for example a median or a mean thickness, of the intermediate layer, a mean or median thickness of the allograft, or both. Soaking, as described herein, in a salt solution, for example a saline solution, for example a single saline solution, can be, for example, independently about: 1, 2, 3, 4, 5, 6, 7, 8, 9, or 10 days, or from about 4 or about 4.5 days to about 7 days, or about 4 or about 4.5 days to about 8 days, where a day is 24 hours. Soaking for in the saline solution for about 4 or 4.5 days to about 7 days, for example, followed by soaking in a water solution for about 1, 2, or 3 days, yields several unexpected and superior results. For example, prolonged—for example for at about 4 days or about 4.5 days to least about 7 days—soaking, for example is a salt or saline solution—which was expected to be destructive to the allograft, for example causing partial or complete separation between at least two layers of the allograph, followed by soaking for up to 3 days in a water solution, resulted in an allograft with a substantially increased thickness and an intermediate layer with substantially increased thickness but substantially no damage, for example, substantially no separation of the allograft layers. This was surprising and superior, for example, because soaking skin in water and/or an aqueous saline solution, which can be analogous to soaking an allograft in water and/or an aqueous saline solution, for up to a combined total of about 10 or about 11 days, would be expected to damage and/or degrade the human's skin and would have been expected by extension to degrade the allograft. The fetal allografts herein, can surprisingly and superiorly:

1) be soaked for a long period of time without substantial damage, or without damage, for example without structural damage, for example without substantial separation of or without separation of the layers in the allograft, as evaluated, for example, by visual analysis;
2) have, for the isolated and purified mammalian, for example human, fetal allografts, an increased or substantially increased thickness of the resulting allograft, the intermediate layer therein, or both—for example, 1 a thickness of the intermediate layer of the allograft that ranges from 661 micrometers to about 2000 micrometers; for example a thickness of the intermediate layer of the allograft that ranges from about 961 micrometers to about 2350 micrometers; or both which can be measured, for example, by a micrometer or with a microscope or both;
3) can surprisingly, for the isolated and purified mammalian, for example human, fetal allografts, retain one or more substances or compounds beneficial to a wound healing or that promote or facilitate wound healing that were present in the allograft before soaking remain present in the allograft after the soaking, for example, and individually, at least about: 80%, 85%, 90%, 95%, 97%, 98%, or 99% of a compound present before soaking is retained in the allograft after soaking, which can be measured and calculated on an amount (weight) of compound or substance present before soaking an amount (weight) of compound present after soaking according to a formula: ((weight compound present in allograft before soaking/weight compound present in allograft after soaking)*100%) where the one or more compounds or substances can be, for example, one or more growth factors, such as fibroblast growth factors, epidermal growth factor, transforming growth factor (TGF) beta, platelet-derived growth factors, etc.; one or more extracellular matrix molecules such as collagens, elastins, proteoglycans, non-proteoglycan polysaccharides, fibronectins, laminins, nidogens, etc.; and/or one or more other biomolecules, such as cytokines (e.g., interleukins, TGF-beta, etc.), metalloproteinases, tissue inhibitors of metalloproteinases (TIMPs), etc.;—and optionally while substantially removing, or removing blood and/or blood components such as hemoglobin for example, the amount of hemoglobin remaining in an isolated and purified fetal allograft after soaking and drying, optionally vacuum drying, can be about 1 ng to about 30 ng; about 1 ng to about 20 ng; about 1 ng to about 10 ng; about 1 ng to about 50 ng; about 1 ng to about ng; about 1 ng to about 30 ng; about 1 ng to about 20 ng; about 1 ng to about 15 ng; about 1 ng to about 10 ng; about 1 ng to about 5 ng; or less than or equal to about: 60 ng, 50 ng, 40 ng, 30 ng, 20 ng, 15 ng, 13 ng, 10 ng, or 5 ng per mg of dry isolated and purified human fetal allograft;

4) can, for the isolated and purified mammalian, for example human, fetal allografts, for example, when contacted with a wound, surprisingly increase or substantially increase the rate of healing of the wound—for example, the wound can heal in about 4, about 5, about 6, about 7, or about 8 months,—which can be about: 1, 2, 3, 4, 5, 6, or more months faster than the healing of an uncontacted wound, or a wound contacted an otherwise comparable mammalian, for example human, fetal allograft that was soaked for a smaller individual or combined duration of time for example, 1.5 days or about 2 days or about 3 days in total, had a smaller comparative average or mean thickness of the intermediate layer, a smaller comparative average or mean thickness of the human fetal allograft, or both; or a combination of these; or 5) any combination of 1), 2), 3), and 4).

Also surprisingly and superiorly, the allograft, soaked for example from about 4 or about 4.5 days to about 7 or about 8 days is a salt solution, followed by soaking for about 1 to about 3 days in a water solution, can retain one more substances such as one or more growth factors, such as fibroblast growth factors, epidermal growth factor, transforming growth factor (TGF) beta, platelet-derived growth factors, etc.; one or more extracellular matrix molecules such as collagens, elastins, proteoglycans, non-proteoglycan polysaccharides, fibronectins, laminins, nidogens, etc.; and/or one or more other biomolecules, such as cytokines (e.g., interleukins, TGF-beta, etc.), metalloproteinases, tissue inhibitors of metalloproteinases (TIMPs), etc. This is surprising and superior. In certain instances, the soaking includes a salt which can be a sodium salt, a potassium salt, a lithium salt, a calcium salt, a magnesium salt, a manganese salt, a copper salt, a zinc salt, an organic salt, an inorganic salt, a chloride salt, a sulfate salt, a carbonate salt, a phosphate salt, an iodide salt, a bromide salt, an acetate salt, or any combination thereof. In some instances, the salt can be sodium chloride, potassium chloride, lithium chloride, calcium chloride, magnesium chloride, manganese chloride, copper chloride, zinc chloride, sodium sulfate, potassium sulfate, lithium sulfate, calcium sulfate, magnesium sulfate, manganese sulfate, copper sulfate, zinc sulfate, sodium carbonate, potassium carbonate, calcium carbonate, magnesium carbonate, manganese carbonate, copper carbonate, zinc carbonate, sodium phosphate, potassium phosphate, lithium phosphate, calcium phosphate, magnesium phosphate, manganese phosphate, copper phosphate, zinc phosphate, sodium acetate, potassium acetate, lithium acetate, calcium acetate, magnesium acetate, manganese acetate, copper acetate, zinc acetate, or any combination thereof. The concentration of the salt in the aqueous salt solution may range solution range from about 0.01 M to about 4.0 M; or about 0.1 M, or about 1.0 M, or about 1.5 M, or about 2.0 M, or about 2.5 M, or about 3.0 M, or about 3.5 M; or about 0.6 g salt per 100 mL of water; or about 0.7 g of salt per 100 mL of water; or about 0.8 g of salt per 100 mL of water; or about 0.9 g of salt per 100 mL of water; or about 1.0 g of salt per 100 mL; or about 1.1 g of salt per 100 mL; or about 1.2 g of salt per 100 mL; or about 1.3 g of salt per 100 mL; or about 1.4 g or salt per 100 ml of water; or about 1.5 g of salt per 100 mL of water; or about 1.6 g of salt per 100 mL of water; or from about 0.6 g of salt per 100 mL of water to about 1.6 g of salt per 100 mL of water. The solutions can, optionally, contain one or more further ingredients.

The human fetal tissue allograft precursor (for example, prior to soaking), can be harvested from placental tissue, for example, after birth. The reduction in damage during production can result in increased efficacy in treating of subjects with lesions requiring said allografts.

Placenta Collection and Preparation

In some instances, any process comprised herein can be used in conjunction with placental tissue that may be collected from a human or other mammal, including but not limited to a primate, artiodactyl, perissodactyl, cow, bison, horse, pig, goat, or the like, and this can produce a mammalian fetal tissue allograft. Placenta may be recovered from a mammal such as a human during a full-term or near full-term Cesarean (C-section) birth. Donor mothers, or the donated placental tissue itself may in certain instances, be screened for environmental or biological factors which may pose undesirable risks to technicians preparing the fetal allografts, clinicians using the fetal allografts, or patients receiving the fetal allografts. Examples of biological factors which may pose undesirable risks include infectious agents such as prions, bacteria, and viruses. Testing may include, but are not limited to: PCR, RT-PCR, culture testing, southern blots, northern blots, western blots, sequencing, antibody tests such as ELISA tests, FISH tests, and the like. and the like. Examples of viruses that may tested include, but are not limited to HIV-1, HIV-2, HTLV-1, HTLV-2, hepatitis A, B, and C viruses, and herpes viruses such as HHV 1, 2, 3, 4, 5, 6, 7 and 8. Examples of bacteria that may be tested include, but are not limited to: *Treponema pallidum, Neisseria gonorrhoeae, Chlamydia trachomatis*, group A *Streptococcus* species, and *staphylococcus* bacteria. The placenta of a donor mother may be considered acceptable based on review of her health information or any screening test results.

The placental tissue may be subject to washing to remove blood remnants or other debris from the surface or interior of an unseparated amnion/chorion, a separated amnion, or a separated chorion in the presence of a suitable washing medium by any number of methods, including but not limited to flushing, immersing, perfusing, soaking, or agitating in the presence or absence of pressure or vacuum. In some cases, the agitating is performed using a rocker, shaker, stir plate, rotating mixer, or other equipment capable of agitating. In some cases, an unseparated amnion/chorion, a separated amnion, or a separated chorion may be washed before, during, or after any step or any combination of steps selected from dissecting, separating, pretreating, cutting, and perforating. For example, in some cases, an unseparated amnion/chorion, a separated amnion, or a separated chorion may be washed before or after being perforated.

In certain instances, steps intended to remove material (e.g., blood remnants or other debris) from the surface or loosen material from the interior of an unseparated amnion/chorion, a separated amnion, or a separated chorion by any number of methods, including but not limited to picking, dabbing, rubbing, or massaging with a fingertip, swab, or gauze. Forceps may be used to remove blood clots. Pretreatment may be performed manually. In some embodiments, the pretreating is performed in the presence of a suitable washing medium. In some embodiments, an unseparated amnion/chorion, a separated amnion, or a separated chorion may be pre-treated before, during, or after any step or any combination of steps selected from dissecting, separating, cutting, perforating, and washing.

However, using the production steps described herein, a typical step of exposure of the fetal allografts to certain detergents may be omitted while yielding surprisingly improved results. Typically, these detergents include N-lauroylsarcosinate, n-octyl-b-D-gluc,opyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, a polyoxyethylene sorbitol ester, N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, a polyoxyethylene sorbitol ester, or any combination thereof, or any combination thereof.

In certain instances, the step or steps to remove material results in a fetal allograft that does not comprise or does not substantially comprise a blood clot, a blood component, an epithelial cell, a fibroblast, a trophoblast, a blood cell, or any combination thereof.

The placental tissue may be soaked in a NaCl of about 0.45%, about 0.9%, about 1.8%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, or at a w/v concentration of NaCl less than any of the concentrations listed above, greater than any of the concentrations listed above, of at least any of the concentrations listed above, or a range bounded by any two of the concentrations listed above, such as about 0.45% to about 5%, about 5% to about 10%, about 10% to about 20%, about 20% to about 30%, about 20% to about 25%, about 25% to about 30%, about 30% to about 36%, about 0.45% to about 15%, about 15% to about 33%, or about 15% to about 36%. In certain instances, the saline solution is a physiological saline solution of 0.9% NaCl. In certain instances, the NaCl or other salt solution may be expressed as a molarity such as from about 0.01 M to about 4.0 M; or about 0.1 M, or about 1.0 M, or about 1.5 M, or about 2.0 M, or about 2.5 M, or about 3.0 M, or about 3.5 M. The concentration of the salt in the aqueous salt solution may range solution range from about 0.01 M to about 4.0 M; or about M, or about 1.0 M, or about 1.5 M, or about 2.0 M, or about 2.5 M, or about 3.0 M, or about 3.5 M; or about 0.6 g salt per 100 mL of water; or about 0.7 g of salt per 100 mL of water; or about 0.8 g of salt per 100 mL of water; or about 0.9 g of salt per 100 mL of water; or about 1.0 g of salt per 100 mL; or about 1.1 g of salt per 100 mL; or about 1.2 g of salt per 100 mL; or about 1.3 g of salt per 100 mL; or about 1.4 g or salt per 100 ml of water; or about 1.5 g of salt per 100 mL of water; or about 1.6 g of salt per 100 mL of water; or from about 0.6 g of salt per 100 mL of water to about 1.6 g of salt per 100 mL of water. The solutions can, optionally, contain one or more further ingredients.

In other instances, the salt is a potassium salt, a calcium salt, a magnesium salt, a manganese salt, a copper salt, a zinc salt, an organic salt, an inorganic salt, a chloride salt, a sulfate salt, a carbonate salt, a phosphate salt, an iodide salt, a citrate salt, a salt of an amino acid, for example glutamine or arginine, or any combination thereof.

In some instances, during the preparation of the isolated and purified mammalian, for example human, fetal allograft, the allograft-in-the-process-of-being prepared can be washed or soaked, for example, in a solution, for example an aqueous solution, comprising an amino acid or a salt thereof, for example glutamine or arginine or a salt of any of these, or hemoglobin or a salt thereof. The concentration of these materials can be, for example, about 0.001 M, about 0.01 M, about 0.1 M, about 1 M, about 2 M, about 3 M, about 4 M, about 5 M, or about 10 M. The washing or soaking can be, for example, for about 1 hour to about 7 or about 8 days, for example about: 1 hour, about 3 hours, about 5 hours, about 10 hours, about 15 hours, about 24 hours, about 2 days, about 3 days, about 4 days, about 5 days, or about 6 days, and can be at any temperature recited herein—for example about: 4, 5, 6, 7, 8, 9, 10, 11, 12, 13, 14, 15, 16 17, 18, 19, 20, 21, 22 23, 24, 25, 26, 27, 28, 29 or 30 degrees C.

In some cases, the saline wash (or soak) and the aqueous wash (or soak) can be reversed. For example, in some cases, the aqueous wash can be first and the saline wash can be second. In some cases, the saline wash can be omitted. In some cases, the aqueous wash can be omitted.

In certain cases, the NaCl solution may further comprise one or more other ingredients, such as phosphate, potassium, magnesium, calcium, dextrose, glucose, citrate, lactate, tris, HEPES, etc. Other suitable washing mediums include water (e.g., purified or sterile), Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (FIBS), Gey's balanced salt solution (GBSS), cell culture mediums (e.g., Delbecco's Modified Eagle Medium (DMEM), Minimum Essential Media (MEM), etc.), hydrogen peroxide solutions, sodium hypochloride solutions, or other medium suitable for washing tissue.

The soaking of the tissue in an aqueous salt solution such as NaCl and water may be for a certain time duration such as about 1, 2, 3, 4, 5, 6, 7, 8, 9, 10, 11, 12, 13, 14, 15, 16, 17, 18, 19, 20, 21, 22, or 23 hours, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days or some time duration therein. In certain instances, the placental material is soaked for from about 4.5 days or about 5 days to about 7 days.

In certain cases, a subsequent soaking may take place in water. The duration may be within the ranges for soaking in the aqueous salt solution step. In certain instances, the duration is from or between about: 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71 or 72 hours. In certain instances, the duration is about 32 hours. In certain instances, the water is sterile, in certain instances, the water is distilled, in certain instances, the water is deionized.

During the soaking processes, soaking may be done at a desired temperature wherein the soaking solution maintains a liquid form. In certain cases, the soaking temperature is at or below about: 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., C, 4° C., 3° C., 2° C., or 1° C. Soaking temperatures can individually be different or the same, for example, for a salt solution or saline soak and a water soak.

The fetal allograft may be vacuum dried in certain cases. The vacuum drying may be done at a temperature from about: 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., or 10° C.

In certain cases, during the preparation, the isolated and purified mammalian, for example human, fetal allograft may be marked to aid in application by a health practitioner and or cut, etched, perforated, textured, or otherwise shaped to create pre-made attachment points. Such modification may aid in increasing visibility of the one or more pre-made attachment points; guiding placement of the isolated and purified mammalian, for example human, fetal allograft onto or into recipient or subject tissue, for example a wound of a subject; determine an orientation of the isolated and purified mammalian, for example human, fetal allograft; or assisting with placement of one or more nerve ends at a measured distance within the isolated and purified mammalian, for example human, fetal allograft.

Further, the isolated and purified mammalian, for example human, fetal allograft may be shaped or processed such that has a specific height and length, and thickness. For example, the height, the length, or the height and the length may independently be about: 1, 2, 3, 4, 5, 6, 7, 8, 9, 10, 11, 12, 13, 14, 15, 16, 17, 18, 19, or 20 cm. In some cases, a fetal allograft may contain an amnion with an average thickness of about: 50 microns to 500 microns; 70 microns to 180 microns, or 80 microns to 130 microns. In some cases, a fetal allograft may contain an amnion with an average thickness of about: 50 microns, 60 microns, 70 microns, 80 microns, 90 microns, 100 microns, 110 microns, 120 microns, 130 microns, 140 microns 150 microns, 160 microns, 170 microns, 180 microns, 190 microns 200 microns, 210 microns, 220 microns, 230 microns, 240 microns, 250 microns, 260 microns, 270 microns, 280 microns, 290 microns, 300 microns, 310 microns, 320 microns, 330 microns, 340 microns, 350 microns, 360 microns, 370 microns, 380 microns, 390 microns, or 400 microns. In some cases, a fetal allograft may contain a chorion with an average thickness of about: 100 microns to 500 microns; 150 microns to 300 microns, or 180 microns to 250 microns. In some cases, a fetal allograft may contain a chorion with an average thickness of about: 100 microns, 110 microns, 120 microns, 130 microns, 140 microns, 150 microns, 160 microns, 170 microns, 180 microns, 190 microns, 200 microns, 210 microns, 220 microns, 230 microns, 240 microns, 250 microns, 260 microns, 270 microns, 280 microns, 290 microns, 300 microns, 310 microns, 320 microns, 330 microns, 340 microns, 350 microns, 360 microns, 370 microns, 380 microns, 390 microns, or 400 microns.

The isolated and purified mammalian, for example human, fetal allograft may be stored in a container after being dried or dehydrated or vacuum dried or dehydrated, such as an envelope, shaker, glass container, metal container, plastic bag, a plastic wrap, a plastic tube, a pouch, and the like. In certain instances, the isolated and purified mammalian, for example human, fetal allograft may be stored in a container with the addition of a medium or preservation medium that without being limited, can be for example water, a saline solution, petrolatum, petroleum jelly, Vaseline, soft paraffin, glycerol, or Ringer's solution.

In another embodiment, a tissue, sheet, or composition is stored at refrigeration temperature for a limited time.

In certain instances, after processing, the stored isolated and purified mammalian, for example human, fetal allograft does not comprise or does not substantially comprise a blood clot, a blood component, hemoglobin, a maternal decidua cell an epithelial cell, a fibroblast, a trophoblast, a blood cell, or any combination thereof. In certain instances, after processing the stored isolated and purified mammalian, for example human, fetal allograft fetal allograft may comprise one of: a human epidermal growth factor, Syndecan-1, MMP-9 (matrix metalloproteinase-9), TIMP-1 (Tissue Inhibitor of metalloproteinase-1), LAP (surrogate for transforming growth factor-beta1, TGF-beta1), Cystatin C, Galectin-3, BMP-2 (Bone Morphogenic Protein-2), M-CSF (macrophage colony stimulating factor 1), sICAM-1 (soluble intracellular adhesion molecule-1), and IL-37 (Interleukin-37), or any combination thereof.

In come embodiments, the isolated and purified mammalian, for example human, fetal allografts herein can further comprises at least one of isolated and purified: glutamine, a salt thereof, arginine, a salt thereof, or any combination thereof. These can be present in amounts ranging, individually, from about 1 ng to about 100 micrograms, for example about 10 ng, about 20 ng, about 30 ng, about 40 ng, about 50 ng, about 60 ng, about 70 ng, about 80 ng, about, per mg of dry isolated and purified mammalian, for example human, fetal allografts.

In some cases, the isolated and purified mammalian, for example human, fetal allograft may be sterilized after processing. For example, the allograft can be sterilized by gamma radiation. In another example, the allograft can be sterilized by an ethylene oxide gas treatment, a thermal treatment with moist heat, a beta-propiolactone treatment, a chemical processing treatment, an antibiotic soak, or any combination thereof.

Administering and Treatment

In some aspects, disclosed herein are methods of administering a mammalian fetal allograft such as a human fetal allograft as described herein to a subject who can be a subject in need thereof. In some cases, a method of treating or preventing a condition can comprise administering a composition described herein.

In some aspects, a subject can be a subject in need thereof. In some aspects, a subject can have a medical condition such as a wound, a diabetic ulcer, a burn, a tissue damage associated with a surgical injury, a laceration, an incision, an abrasion, an avulsion, a contusion, a penetrating wound, an ulcer, or any combination thereof. In some aspects, administering compositions as described herein can stop the progression or prevent the occurrence of a medical condition.

In some aspects, administering can comprise a topical administration, a subcutaneous administration, an intramuscular administration, an intranasal administration, an oral administration, or intradermal administration.

In some aspects, a fetal allograft can be administered to a subject with a specific mixture of active ingredients and inactive components, diluents, or excipients, in a particular configuration, and apportioned into a treatment dose to be delivered.

In some cases, an amount of fetal allograft may vary with the location of administration and any substance(s) used as a co-therapy. In some aspects, a dosage regimen can be determined by an attending physician and clinical factors. In some aspects, a treatment of a subject can depend upon many factors, including a subject's size, body surface area, age, sex, general health, and any other drugs being administered concurrently, or any combination thereof.

In some aspects, a range of a fetal allograft can comprise an allograft having a height and length, independently, of about: 1, 2, 3, 4, 5, 6, 7, 8, 9, 10, 11, 12, 13, 14, 15, 16, 17, 18, 19, or 20 cm. In some instances, the allograft may have an average thickness that ranges from about 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 2020, 1030, 1040, 1050, 1060, 1070, 1080, 1090, 2000, 2010, 2020, 2030, 2040, 2050, 2060, 2070, 2080, 2090, 3000 or more micrometers or some derivation therein such as between 961 micrometers to about 2350 micrometers.

In some embodiments, a thickness of an isolated and purified fetal allograft can range from about: 961 µm to 2350 µm, 980 µm to 2300 µm, 1000 µm to 2200 µm, 1100 µm to 2000 µm, 1200 µm to 1800 µm, 1100 µm to 1500 µm, or 1000 µm to 2350 µm as measured by a micrometer. In some cases, an average thickness of an isolated and purified fetal allograft can be about: 961 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, 2000 µm, 2010 µm, 2020 µm, 2030 µm, 2040 µm, 2050 µm, 2060 µm, 2070 µm, 2080 µm, 2090 µm, 2100 µm, 2110 µm, 2120 µm, 2130 µm, 2140 µm, 2150 µm, 2160 µm, 2170 µm, 2180 µm, 2190 µm, 2200 µm, 2210 µm, 2220 µm, 2230 µm, 2240 µm, 2250 µm, 2260 µm, 2270 µm, 2280 µm, 2290 µm, 2300 µm, 2310 µm, 2320 µm, 2330 µm, 2340 µm, or 2350 µm as measured by a micrometer.

In some embodiments, a thickness of the intermediate layer of an isolated and purified fetal allograft can range from about: 661 µm to 2000 µm, 700 µm to 1900 µm, 800 µm to 1700 µm, 900 µm to 1500 µm, 1000 µm to 1400 µm, 700 µm to 1400 µm, or 850 µm to 1600 µm as measured by a micrometer. In some cases, an average thickness of the intermediate layer of an isolated and purified fetal allograft can be about: 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, or 2000 µm as measured by a micrometer.

Co-Therapies

In some aspects, disclosed herein are methods of administering an isolated and purified mammalian, for example human, fetal allograft to a subject, optionally in combination with another treatment or therapy. In some aspects, a method can further comprise administering one or more additional therapeutics. In some aspects, one or more additional therapeutics can be administered concurrently. In some aspects, one or more additional therapeutics can be administered consecutively. In some cases, an additional therapeutic can comprise a gas therapy such as surgery, radiation therapy, a debridement, a cryosurgery, a thermotherapy, immunotherapy such as an immunostimulant or an immunosuppressive, a hormone therapy, a growth factor therapy, a pharmaceutical agent, or a combination thereof.

In some aspects, one or more additional therapeutics administered can comprise, a ventilator, an Extracorporeal Membrane Oxygenation (ECMO) machine, nitric oxide, oxygen, saline, interfering RNA therapies, a medicament, a stem cell, or any combination thereof.

In some aspects, when an additional therapy is a pharmaceutical agent, the pharmaceutical agent included in a pharmaceutical composition, which can be in the form of a fixed dose combination drug which comprises the additional therapy and the isolated and purified mammalian, for example human, fetal allograph.

In some aspects, a pharmaceutical agent may comprise an antibiotic, an antiviral, an antiparasitic, a diuretic, an antibiotic, an antiviral, or a combination thereof. In some cases, an antibiotic may comprise a penicillin, a cephalosporin, a tetracycline, an aminoglycoside, a macrolide, clindamycin, a sulfonamide, a trimethoprim, a metronidazole, a quinolone, or a nitrofurantoin. An antiviral may comprise an acyclovir, peramivir, zanamivir, oseltamivir phosphate, remdesivir, baloxavir marboxil, a salt of any of these or any combination thereof.

In some cases, the pharmaceutical agent may comprise a nitrate, nitroglycerin, nitric oxide, nitric oxide generating components, nitrite salts, nitrate salts, sodium nitrates, potassium nitrates, vitamin C, ascorbic acid, L-arginine, L-citrulline, vitamin B12, magnesium ascorbate, sodium ascorbate, potassium ascorbate, antihypertensive agents, diuretics, salts thereof, or any combination thereof.

In some cases, the pharmaceutical agent may comprise a phosphodiesterase inhibitor such as sildenafil, tadalafil, vardenafil, avanafil, mirodenafil, udenafil, iodenafil, derivatives of these, salts of these, or any combinations thereof.

In some cases, a pharmaceutical agent may comprise a phosphodiesterase 5 inhibitor, a beta-blocker, an ACE inhibitor, an angiotensin II receptor antagonist, a calcium channel blocker, an alpha blocker, a cancer chemotherapeutic, a steroid, an anticoagulant, a platelet inhibitor, an immunomodulator, a pharmaceutically acceptable salt of any of these, or any combination thereof. In some cases, an pharmaceutical ingredient or salt thereof may comprise a potassium channel blocker such as dalfampridine or a salt thereof.

In certain instances, an angiotensin 2 receptor antagonist may comprise candesartan cilexetil, eprosartan mesylate, irbesartan, losartan, telmisartan, valsartan, a salt of these, or any combination thereof.

In some instances, an anticoagulant may comprise dalteparin, enoxaparin, fondaparinux, heparin, warfarin, a salt of these, or any combination thereof.

In some instances, a platelet inhibitor may comprise aspirin, cilostazol, clopidogrel, dipyramidamole, prasugrel, ticlopidine, a salt of these, or any combination thereof. In some instances, a co-therapy can include an antihypertensive such as clonidine, doxazosin mesylate, hydralazine, methyldopa, minoxidil, phenoxybenzamine, phentolamine mesylate, prazosin, terazosin, a salt of these or any combination thereof.

In some instances, a beta blocker such as acebutolol, atenolol, betaxolol, bisoprolol, carvedilol, labetalol, metoprolol, nadolol, nebivolol, pindolol, propranolol, sotalol, timolol, a salt of these or any combination thereof. In some instances, a co-therapy can include a calcium channel blocker such as amlodipine besylate, bepridil, diltiazem, felodipine, isradipine, nicardipine, nifedipine, nisoldipine, verapamil, a salt of these or any combination thereof.

In some cases, an additional therapy may be an angiogenesis promoting therapy such as vascular endothelial growth factor (VEGF), a fibroblast growth factor (FGF) such as FGF1 to FGF28, an Ephrin such as Ephrin-B2 or EphB4, a keratinocyte growth factor, a transforming growth factor such as TGF-α or TGF-β, an angioprotein, a salt of these, a derivative of these, or any combination thereof.

In certain instances, a the additional therapy, given as part of a co-therapy, can include an anti-viral drug, such as, acyclovir, adefovir, amantadine, amprenavir, umifenovir, atazanavir, baloxavir, bictegravir, boceprevir, bulevirtide, bidofovir, cidofovir, cobicistat, combivir, daclatasvir, darunavir, delavirdine, didanosine, docosanol, dolutegravir, doravirine, edoxudine, efavirenz, elvitegravir, emtricitabine, enfuvirtide, entecavir, etravirine, famciclovir, fomivirsen, fosamprenavir, foscarnet, ganciclovir, ibacitabine, idoxuridine, imiquimod, imunovir, indinavir, lamivudine, letermovir, lopinavir, loviride, maraviroc, methisazone, moroxydine, methisazone, moroxydine, nelfinavir, nevirapine, nexavir, nitazoxanide, norvir, nseltamivir, penciclovir, peramivir, pleconaril, podophyllotoxin, raltegravir, remdesivir, ribavirin, rilpivirine, rimantadine, ritonavir, saquinavir, simeprevir, sofosbuvir, taribavirin, telaprevir, telbivudine, tenofovir, trifluridine, tromantadine, tromantadine, umifenovir, valaciclovir, valganciclovir, vicriviroc, vidarabine, zalcitabine, zanamivir, chloroquine, hydroxychloroquine, ivermectin, a corticosteroid, losartan, a steroid, an anti-inflammatory, a cytokine storm inhibitor, methylprednisolone, a salt of any of these, or any combination thereof. In some aspects, a cytokine storm inhibitor can comprise a chemokine inhibitor, a compound that targets a cholinergic anti-inflammatory pathway, a platelet activating factor (PAF) inhibitor, a resolvin, a lipoxin, a protectin, a COX-2 inhibitor, a compound targeting a chemokine, a compound targeting a T-reg cell, a prostaglandin, a prostaglandin E2 cyclooxygenase inhibitor, or any combination thereof. In some aspects, an anti-inflammatory can comprise aspirin, ibuprofen, naproxen, celecoxib, diclofenac, diflunisal etodolac, famotidine/ibuprofen, flurbiprofen, indomethacin, ketoprofen, mefenamic acid, meloxicam, nabumetone, oxaprozin, piroxicam, sulindac, celecoxib, a salt of any of these, or any combination thereof. In some aspects, a corticosteroid can comprise a glucocorticoid or a mineralocorticoid. In some aspects, a corticosteroid can comprise prednisone, prednisolone, triamcinolone, triamcinolone, methylprednisolone, dexamethasone, cortisol (hydrocortisone), cortisone, prednisone, prednisolone, methylprednisolone, dexamethasone, betamethasone, triamcinolone, fludrocortisone acetate, deoxycorticosterone acetate, corticosterone, aldosterone, deoxycorticosterone, fludrocortisone, prednisolone, a salt of any of these, or any combination thereof.

In some cases, a co-therapeutic dose regimen can be administered for a duration of about 1 week, about 2 weeks, about 3 weeks, about 4 weeks, about 6 weeks, about 7 weeks, about 8 weeks, about 9 weeks, about 10 weeks, or about 12 weeks. In some cases, a dose regimen can be administered for a duration of about 1 month, about 2 months, about 3 months, about 4 months, about 6 months, about 7 months, about 8 months, about 9 months, about 10 months, or about 12 months. In some cases, a dose regimen can be administered for a duration of about 1 year, about 2 years or more than about 3 years.

In some instances, the administering comprising contacting a wound of a subject or a subject in need thereof.

In some aspects, disclosed herein are methods of use for co-therapy compositions as disclosed herein. In some aspects, a daily oral dosage regimen can be from about 0.1 milligram per kilogram (mg/kg) to about 80 mg/kg of total body weight, from about 0.2 mg/kg to about 30 mg/kg, or from about 0.5 mg/kg to about 15 mg/kg. In some aspects, a daily parenteral dosage regimen can comprise from about 0.1 mg/kg to about 10,000 mg/kg of total body weight, from about 0.2 mg/kg to about 5,000 mg/kg, or from about 0.5 mg/kg to about 1,000 mg/kg. In some aspects, a daily topical dosage regimen can be from about 0.1 mg to about 500 mg. In some aspects, a daily inhalation dosage regimen can be from about 0.01 mg/kg to about 1,000 mg/kg per day. In some aspects, an optimal quantity and spacing of individual dosages of a composition can be determined by a nature and extent of a condition being treated, a form, route and site of administration, and a particular subject being treated, and that such optimums can preferably be determined by a method described herein. In some aspects, a number of doses of compositions given per day for a defined number of days, can be ascertained by those skilled in the art using conventional course of treatment determination tests. In some aspects, a dosage regimen can be determined by an attending physician and other clinical factors. In some aspects, dosages for any one subject can depend upon many factors. In some aspects, factors affecting dosage can comprise a subject's size, body surface area, age, a particular compound to be administered, sex, time and route of administration, general health, other drugs being administered concurrently or any combination thereof. In some aspects, progress can be monitored by periodic assessment.

In some aspects, a co-therapy described herein can be administered one or more days to a subject in need thereof. In some aspects, administration can occur for about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or about 31 days. In some aspects, administration can occur for about: 1, 2, 3, 4, 5, 6, 7, 8, 9, 10, 11, 12, 13, 14, 15, 16, 17, 18, 19, 20, 21, 22, 23, or about 24 months. In some aspects, administration can occur for about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 or more years. In some cases, administration can occur for life. In some aspects, a pharmaceutical composition described herein can be administered on 2, 3, 4, 5, 6, 7, 8, 9, 10, 11, 12, 13, 14, 15, 16, 17, 18, 19 or 20 or more days. In some cases, a composition described herein can be administered on consecutive days or on nonconsecutive days. In some cases, a composition described herein can be administered to a subject more than one time per day. In some instances, a composition described herein can be administered to a subject: 1, 2, 3, 4, 5, 6, 7, 8, 9, or 10 or more times per day.

In some aspects, a regimen as a regular administration of a pharmaceutical agent can be in a range of 1 µg to 10 mg. In some aspects, a regimen as a regular administration of a pharmaceutical composition can be in a range of $10^2$ units to $10^{10}$ units per day, week or month. In some aspects, if a regimen comprises a continuous infusion, it can also be in a range of 1 µg to 10,000 mg of pharmaceutical agent. In certain instances, the range is from 1 mg per kilogram of body weight to 1000 mg per kilogram of body weight. In some aspects, progress can be monitored by periodic assessment.

Kits

Also described herein are kits comprising compositions and formulations described herein. In some cases, a kit can comprise a container that comprises a composition or formulation. In some instances, a kit can comprise instructions for use. In some instances, a container can be a sterile container. In some cases, a container can be a plastic, a glass, or a metal container.

EMBODIMENTS

A number of compositions, and methods are disclosed herein. Specific exemplary embodiments of these compositions and methods are disclosed below. The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed.

Embodiment 1. An isolated and purified mammalian, for example human, fetal allograft, comprising:
an amnion layer and a chorion layer and an intermediate layer positioned between the amnion layer and the chorion layer;
wherein
the amnion layer and the chorion layer and the intermediate layer are substantially unseparated, and wherein the isolated and purified human fetal allograft has:
1) a thickness of the intermediate layer of the isolated and purified human fetal allograft that ranges from 661 micrometers to about 2000 micrometers;
2) the isolated and purified mammalian, for example human, fetal allograft has an average thickness that ranges from about 961 micrometers to about 2350 micrometers; or
3) a combination of 1) and 2); and optionally the isolated and purified mammalian, for example human, fetal allograft further comprises an exogenous amount of: glutamine, a salt thereof, arginine, a salt thereof, or any combination thereof, in an amount ranging from about 1 ng to about 1000 micrograms, for example, about 10 ng, about 50 ng, about 100 ng, about 200 ng, about 300 ng, about 400 ng, about 500 ng, about 1 microgram, about 10 micrograms, about 50 micrograms, about 100 micrograms, about 500 micrograms, or about 750 micrograms.

Embodiment 2. The isolated and purified mammalian, for example human, fetal allograft of embodiment 1, that is sterile.

Embodiment 3. The isolated and purified mammalian, for example human, fetal allograft of embodiment 1 or embodiment 2, that is dehydrated or is hydrated.

Embodiment 4. The isolated and purified mammalian, for example human, fetal allograft of embodiment 3, that is vacuum dehydrated.

Embodiment 5. The isolated and purified mammalian, for example human, fetal allograft of any one of embodiments 1-4, wherein the amnion layer, the intermediate layer, and the chorion layer are unseparated.

Embodiment 6. The isolated and purified mammalian, for example human, fetal allograft of any one of embodiments 1-5, having an average thickness that ranges from about 961 micrometers to about 2350 micrometers.

Embodiment 7. The isolated and purified mammalian, for example human, fetal allograft of any one of embodiments 1-7, which does not substantially comprise maternal decidua cells.

Embodiment 8. The isolated and purified mammalian, for example human, fetal allograft of any one of embodiments 1-7, which does not comprise maternal decidua cells.

Embodiment 9. The isolated and purified mammalian, for example human, fetal allograft of any one of embodiments 1-7, which is substantially not translucent.

Embodiment 10. The isolated and purified mammalian, for example human, fetal allograft of embodiment 10, which is not translucent.

Embodiment 11. The isolated and purified mammalian, for example human, fetal allograft of embodiment 11, wherein translucence is determined by visual inspection that comprises holding the isolated and purified human allograft between a visible light source and a surface having marking(s) and visually detecting whether the marking(s) on the surface are visible through the isolated and purified human fetal allograft.

Embodiment 12. The isolated and purified mammalian, for example human, fetal allograft of any one of embodiments 1-12, wherein the isolated and purified human fetal allograft is not compressed, folded, or both.

Embodiment 13. The isolated and purified mammalian, for example human, fetal allograft of any one of embodiments 1-13, which does not substantially comprise cells.

Embodiment 14. The isolated and purified mammalian, for example human, fetal allograft of embodiment 13, which does not comprise or does not substantially comprise: a cell, a blood clot, a blood component, an epithelial cell, a fibroblast, a trophoblast, a blood cell, or any combination thereof.

Embodiment 15. The isolated and purified mammalian, for example human, fetal allograft of any one of embodiments 1-15, that comprises at least one of: a human epidermal growth factor, Syndecan-1, MMP-9 (matrix metalloproteinase-9), TIMP-1 (Tissue Inhibitor of metalloproteinase-1), LAP (surrogate for transforming growth factor-beta1, TGF-beta1), Cystatin C, Galectin-3, BMP-2 (Bone Morphogenic Protein-2), M-CSF (macrophage colony stimulating factor 1), sICAM-1 (soluble intracellular adhesion molecule-1), and IL-37 (Interleukin-37), or any combination thereof.

Embodiment 16. The isolated and purified mammalian, for example human, fetal allograft of any one of embodiments 1-15, which comprises a marking.

Embodiment 17. The isolated and purified mammalian, for example human, fetal allograft of any one of embodiments 1-16, that comprises one or more pre-made attachment points.

Embodiment 18. The isolated and purified mammalian, for example human, fetal allograft of embodiment 17, wherein the one or more pre-made attachment points comprises one or more etchings, and wherein the one or more etchings are configured to:
 i) increase visibility of the one or more pre-made attachment points;
 ii) guide placement of the isolated and purified mammalian, for example human, fetal allograft onto recipient tissues; determine an orientation of the isolated and purified human fetal allograft;
 iii) assist with placement of one or more nerve ends at a measured distance within the isolated and purified human fetal allograft; or
 iv) any combination thereof.

Embodiment 19. The isolated and purified mammalian, for example human, fetal allograft of any one of embodiments 1-18, which does not substantially comprise hemoglobin, or does not comprise hemoglobin.

Embodiment 20. The isolated and purified mammalian, for example human, allograft of any one of embodiments 1-18, which comprises hemoglobin in an amount ranging from: about 0.001 micrograms to about 50 micrograms; about 0.01 micrograms to about 50 micrograms; about 0.1 micrograms to about 50 micrograms; about 1 microgram to about micrograms; about 1 microgram to about 40 micrograms; about 1 microgram to about micrograms; about 1 microgram to about 20 micrograms; about 1 microgram to about micrograms; about 14 micrograms to about 50 micrograms; about 15 micrograms to about 50 micrograms; about 20 micrograms to about 50 micrograms; about 25 micrograms to about 50 micrograms; about 30 micrograms to about 50 micrograms; about 35 micrograms to about 50 micrograms; about 40 micrograms to about 50 micrograms; or about 45 micrograms to about 50 micrograms; about 1 ng to about 60 ng; about 1 ng to about 50 ng; about 1 ng to about 40 ng; about 1 ng to about 30 ng; about 1 ng to about 20 ng; about 1 ng to about 10 ng; about 1 ng to about 50 ng; about 1 ng to about 40 ng; about 1 ng to about 30 ng; about 1 ng to about 20 ng; about 1 ng to about 15 ng; about 1 ng to about 10 ng; about 1 ng to about 5 ng; or less than or equal to about: 60 ng, 50 ng, 40 ng, 30 ng, 20 ng, 10 ng, or 5 ng; per mg of dry isolated and purified human fetal allograft.

Embodiment 21. The isolated and purified mammalian, for example human, fetal allograft of any one of embodiments 1-20, in the form of a fine powder.

Embodiment 22. The isolated and purified mammalian, for example human, fetal allograft of any one of embodiments 1-21, which has a rectangular or square shape; and which optionally comprises at least one of: an excipient, a diluent, a carrier, a preservative, or any combination thereof.

Embodiment 23. The isolated and purified mammalian, for example human, fetal allograft of embodiment 22, having a height and length, independently, of about: 1, 2, 3, 4, 5, 6, 7, 8, 9, 10, 11, 12, 13, 14, 15, 16, 17, 18, 19, or 20 cm.

Embodiment 24. A kit comprising the isolated and purified mammalian, for example human, fetal allograft of any one of embodiments 1-23, and a container.

Embodiment 25. The kit of embodiment 24, which comprises a marking on the container.

Embodiment 26. The kit of embodiment 25, wherein the marking orients the isolated and purified mammalian, for example human, fetal allograph.

Embodiment 27. The kit of any one of embodiments 24-26, wherein the container is in the form of an envelope, a pouch, or a shaker; or wherein the container comprises a glass, a plastic, a metal, or any combination thereof; or any combination of these.

Embodiment 28. A method, comprising contacting a wound with the isolated and purified human mammalian, for example human, allograft of any one of embodiments 1-23.

Embodiment 29. A method of treating a disease or condition in a subject, comprising treating the disease or condition with a therapeutically effective amount of the isolated and purified mammalian, for example human, fetal allograft of any one of embodiments 1-23.

Embodiment 30. The method of embodiment 29, wherein the disease or condition comprises a wound.

Embodiment 31. The method of any one of embodiments 29 or 30, wherein the wound is selected from the group consisting of an incision, a laceration, an abrasion, an avulsion, a burn, a contusion, a penetrating wound, an ulcer, a diabetic ulcer, a diabetic foot ulcer, and any combination thereof.

Embodiment 32. The method of any one of embodiments 29-31, wherein the treating comprises contacting the wound with the therapeutically effective amount of the isolated and purified mammalian, for example human, allograft.

Embodiment 33. The method of any one of embodiments 29-31, wherein the treating further comprises administering a second therapeutic, and wherein the second therapeutic is administered: consecutively or concurrently; and optionally, wherein the second therapeutic is administered concurrently in a composition comprising the isolated and purified human mammalian, for example human, allograft and the second therapeutic.

Embodiment 34. The method of embodiment 33, wherein the second therapeutic comprises a phosphodiesterase type 5 inhibitor or a pharmaceutically acceptable salt thereof, nitroglycerine, a nitrate, a nitric oxide donor or a pharmaceutically acceptable salt thereof, nitric oxide, an antibiotic or pharmaceutically acceptable a salt thereof, a surgical process, a debridement, or any combination thereof.

Embodiment 35. The method of any one of embodiments 28-34, wherein the method results in a decreased healing time when compared to a healing time when compared to a healing time arising from a comparable method employing an otherwise comparable isolated and purified human fetal allograft wherein in the otherwise comparable isolated and purified mammalian, for example human, fetal allograft:
 i) the amnion layer and the chorion layer were separated and subsequently reattached prior to introduction in a subject;
 ii) the amnion layer and the chorion layer are substantially unseparated or are unseparated, and the otherwise comparable isolated and purified human mammalian, for example human, allograft comprises an intermediate layer having a thickness of about 100 micrometers to about: 660, 650, 640, 630, 620, 610, 600, 590, 580, 570, 560, 550, 540, 530, 520, 510, 500, 490, 480, 470, 460, 450, 425, 400, 375, 350, 325, 300, 275, 250, 225, or 200 micrometers iii) the amnion layer and the chorion layer are unseparated and the otherwise comparable isolated and purified mammalian, for example human, fetal allograft has average thickness from about 100 micrometers to less than about 660 micrometers, from about 100 micrometers to less than about 600 micrometers, from about 100 micrometers to less than about 500 micrometers, from about 100 micrometers to about less than 400 micrometers, or from about 100 micrometers to about less than 300 micrometers; or iv) any combination of ii) and iii).

Embodiment 36. A method of making the hydrated or dehydrated isolated and purified mammalian, for example human, fetal allograft of any one of embodiments 1-23, the method comprising, optionally removing a blood component from a precursor isolated and purified mammalian, for example human, fetal allograft;

optionally removing a blood clot from a precursor isolated and purified mammalian, for example human, fetal allograft;

optionally removing a tissue section from a precursor isolated and purified mammalian, for example human, fetal allograft;

soaking a precursor isolated and purified mammalian, for example human, fetal allograft in an aqueous salt solution for a time period of at least about: 2 days, 3 days, 4 days, 5 days, 6 days, 7 days, 8 days, 9 days, 10 days, 11 days, 12 days, 13 days, 14 days; or from about 2 days to about 14 days; wherein a day is 24 hours; thereby forming a soaked precursor isolated and purified mammalian, for example human, fetal allograft.

Embodiment 37. The method of claim 36, wherein the soaking is for a period of about 7 days.

Embodiment 38. The method of claim 36 or 37, wherein the salt is sodium salt, a potassium salt, a calcium salt, a magnesium salt, a manganese salt, a copper salt, a zinc salt, an organic salt, an inorganic salt, a chloride salt, a sulfate salt, a carbonate salt, a phosphate salt, an iodide salt, or any combination thereof.

Embodiment 39. The method of any one of claims 36-38, wherein a concentration of the salt in the aqueous solution ranges from about 0.01 M to about 4.0 M; or about 0.1 M, or about 1.0 M, or about 1.5 M, or about 2.0 M, or about 2.5 M, or about 3.0 M, or about 3.5 M, or about 0.6 g salt per 100 mL of water; or about 0.7 g of salt per 100 mL of water; or about 0.8 g of salt per 100 mL of water; or about 0.9 g of salt per 100 mL of water; or about 1.0 g of salt per 100 mL; or about 1.1 g of salt per 100 mL; or about 1.2 g of salt per 100 mL; or about 1.3 g of salt per 100 mL; or about 1.4 g or salt per 100 ml of water; or about 1.5 g of salt per 100 mL of water; or about 1.6 g of salt per 100 mL of water; or from about 0.6 g of salt per 100 mL of water to about 1.6 g of salt per 100 mL of water.

Embodiment 40. The method of any one of embodiments 36-39, further comprising, after the soaking, conducting an aqueous rinse, thereby forming a hydrated isolated and purified mammalian, for example human, fetal allograft.

Embodiment 41. The method of embodiment 40, wherein the aqueous rinse is conducted employing: a deionized water, a distilled water, a reverse osmosis purified water, a purified water, tap water, or any combination thereof.

Embodiment 42. The method of any one of embodiments 40-41, wherein the aqueous rinse is conducted for a period of time ranging from about 16 hours to about 72 hours, or about: 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 54, 55, 56, 57, 58, 59, 60, 61, 62, 63, 64, 65, 66, 67, 68, 69, 70, 71, or 72 hours.

Embodiment 43. The method of any one of embodiments 40-42, which forms a hydrated isolated and purified mammalian, for example human, fetal allograft; the method optionally further comprising, after the aqueous rinse, drying the hydrated isolated and purified human fetal allograft, thereby forming a dehydrated isolated and purified human fetal allograft.

Embodiment 44. The method of embodiment 43, wherein the drying comprises vacuum drying.

Embodiment 45. The method of any one of embodiments 40-44, further comprising shaping the hydrated or the dehydrated isolated and purified human fetal allograft.

Embodiment 46. The method of embodiment 45, wherein the shaping comprises: cutting or slicing or tearing or ripping or rending or pulling apart or molding or any combination thereof.

Embodiment 47. The method of any one of embodiments 40-46, further comprising packaging the isolated and purified mammalian, for example human, fetal allograft.

Embodiment 48. The method of embodiment 47, further comprising sterilizing the isolated and purified mammalian, for example human, fetal allograft.

Embodiment 49. The method of any one of embodiments 36-48 wherein the method does not comprise a contacting or a substantially contacting with: N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, a polyoxyethylene sorbitol ester, or any combination thereof.

Embodiment 50. The isolated and purified mammalian, for example human, fetal allograft of any one of embodiments 1-23, that comprises, or that does not comprise, or that does not substantially comprise, at least one of: N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, a polyoxyethylene sorbitol ester, or any combination thereof.

EXAMPLES

Example 1

When placental tissue arrives from the vendor, it has been transported in its natural milieu, including placental blood. This blood will stain the membranes over time. To remove as much of the placental blood as possible, clots were removed from the tissue using forceps. At this point, the membrane was generally a light pink to light brown color, which can necessitate further cleaning. To avoid using detergents, the placental membrane was soaked in 0.9% NaCl (0.9 g NaCl per 100 mL of water) for 7 days at 4° C. This rinsing step yields a membrane that is light yellow to light brown.

Once the membrane was rinsed/soaked, it is transferred to a container with deionized water and soaked for 32 hours at 4° C. The intermediate, or spongy, layer of the placental membrane is highly hydrophilic and will swell (increase thickness) during this soak, providing the final membrane with its characteristic thickness. (conjecture, may or may not want to include: This swelling step provides a layer consisting of a porous, mostly open space.)

The resulting fetal allograft was then vacuum dried while maintaining the membrane at a temperature in a range of from about 10 to 30° C. throughout the vacuum drying process. Application of a vacuum allows water within the membrane to be extracted without baking or freezing.

The resulting allograft was then cut to size. Properly sized allografts were then placed into a Tyvek pouch and sealed using an impulse sealer. This packaged allograft was then placed into a larger Tyvek pouch and sealed.

Once packaged, the allografts were sterilized by gamma sterilization. Each allograft received a gamma radiation dosage of 17.5 kGy. Gamma exposure was validated using a color-changing label.

Example 2

An isolated and purified human fetal allograft was applied to and contacted with a wound of a human patient/subject. The results of the application and its aftermath are shown in FIG. 1.

While preferred aspects of the present disclosure have been shown and described herein, such aspects are provided by way of example only. Numerous variations, changes, and substitutions can occur. It should be understood that various alternatives to the aspects of the disclosure described herein may be employed in practicing the disclosure. It is intended that the following claims define the scope of the disclosure and that methods and structures within the scope of these claims and their equivalents be covered thereby.

What is claimed is:

1. An isolated and purified human fetal allograft, comprising:
   an amnion layer and a chorion layer and an intermediate layer positioned between the amnion layer and the chorion layer;
   wherein
   the amnion layer and the chorion layer and the intermediate layer are substantially unseparated or unseparated, and
   a thickness of the intermediate layer of the isolated and purified human fetal allograft ranges from 661 micrometers to about 2000 micrometers as calculated by a micrometer.

2. The isolated and purified human fetal allograft of claim 1, that is sterile.

3. The isolated and purified human fetal allograft of claim 1, that is dehydrated.

4. The isolated and purified human fetal allograft of claim 3, that is vacuum dehydrated.

5. The isolated and purified human fetal allograft of claim 1, that is hydrated.

6. The isolated and purified human fetal allograft of claim 1, wherein the amnion layer, the intermediate layer, and the chorion layer are unseparated.

7. The isolated and purified human fetal allograft of claim 1, having an average thickness that ranges from about 961 micrometers to about 2350 micrometers.

8. The isolated and purified human fetal allograft of claim 1, which does not substantially comprise maternal decidua cells.

9. The isolated and purified human fetal allograft of claim 1, which does not comprise maternal decidua cells.

10. The isolated and purified human fetal allograft of claim 1, which is substantially not translucent.

11. The isolated and purified human fetal allograft of claim 1, which is not translucent.

12. The isolated and purified human fetal allograft of claim 11, wherein translucence is determined by visual inspection that comprises holding the isolated and purified human allograft between a visible light source and a surface having marking(s) and visually detecting whether the marking(s) on the surface are visible through the isolated and purified human fetal allograft.

13. The isolated and purified human fetal allograft of claim 1, wherein the isolated and purified human fetal allograft is not compressed, folded, or both.

14. The isolated and purified human fetal allograft of claim 1, which does not substantially comprise cells.

15. The isolated and purified human fetal allograft of claim 14, which does not comprise or does not substantially comprise: a cell, a blood clot, a blood component, an epithelial cell, a fibroblast, a trophoblast, a blood cell, or any combination thereof.

16. The isolated and purified human fetal allograft of claim 1, that comprises at least one of: a human epidermal growth factor, Syndecan-1, MMP-9 (matrix metalloproteinase-9), TIMP-1 (Tissue Inhibitor of metalloproteinase-1), Latency Associated Peptide (LAP), Cystatin C, Galectin-3, BMP-2 (Bone Morphogenic Protein-2), M-CSF (macrophage colony stimulating factor 1), sICAM-1 (soluble intracellular adhesion molecule-1), and IL-3 (Interleukin-37), or any combination thereof.

17. The isolated and purified human fetal allograft of claim 1, which comprises a marking.

18. The isolated and purified human fetal allograft of claim 1, that comprises one or more pre-made attachment points.

19. The isolated and purified human fetal allograft of claim 18, wherein the one or more pre-made attachment points comprises one or more etchings, and wherein the one or more etchings are configured to:
   i) increase visibility of the one or more pre-made attachment points;
   ii) guide placement of the isolated and purified human fetal allograft onto recipient tissues; determine an orientation of the isolated and purified human fetal allograft;
   iii) assist with placement of one or more nerve ends at a measured distance within the isolated and purified human fetal allograft; or
   iv) any combination thereof.

20. The isolated and purified human fetal allograft of claim 1, which does not substantially comprise hemoglobin, or does not comprise hemoglobin.

21. The isolated and purified human fetal allograft of claim 1, which comprises hemoglobin in an amount ranging from: about 0.001 micrograms to about 50 micrograms; about 0.01 micrograms to about 50 micrograms; about 0.1 micrograms to about 50 micrograms; about 1 microgram to about 50 micrograms; about 1 microgram to about 40 micrograms; about 1 microgram to about 30 micrograms; about 1 microgram to about 20 micrograms; about 1 microgram to about 10 micrograms; about 14 micrograms to about 50 micrograms; about 15 micrograms to about 50 micrograms; about 20 micrograms to about 50 micrograms; about 25 micrograms to about 50 micrograms; about 30 micrograms to about 50 micrograms; about 35 micrograms to about 50 micrograms; about 40 micrograms to about 50 micrograms; about 45 micrograms to about 50 micrograms; about 1 ng to about 50 ng; about 1 ng to about 40 ng; about 1 ng to about 30 ng; about 1 ng to about 20 ng; about 1 ng to about 10 ng; about 1 ng to about 50 ng; about 1 ng to about 40 ng; about 1 ng to about 30 ng; about 1 ng to about 20 ng;

about 1 ng to about 15 ng; about 1 ng to about 10 ng; about 1 ng to about 5 ng; or less than or equal to about: 60 ng, 50 ng, 40 ng, 30 ng, 20 ng, 10 ng, or 5 ng per mg of dry isolated and purified human fetal allograft.

22. The isolated and purified human fetal allograft of claim 1, which has a rectangular shape; a square shape; a cylindrical shape; a circular shape; a conical shape; or is in the form of a sheet.

23. The isolated and purified human fetal allograft of claim 22, in the form of a sheet, having a height and length, independently, of about: 1, 2, 3, 4, 5, 6, 7, 8, 9, 10, 11, 12, 13, 14, 15, 16, 17, 18, 19, or 20 cm.

24. A kit comprising the isolated and purified human fetal allograft of claim 1, and a container.

25. The kit of claim 24, which comprises a marking on the container.

26. The kit of claim 25, wherein the marking orients the isolated and purified human fetal allograft.

27. The kit of claim 26, wherein the container is in the form of an envelope, a pouch, or a shaker; or wherein the container comprises a glass, a plastic, a metal, or any combination thereof; or any combination of these.

28. A method, comprising contacting a wound with the isolated and purified human fetal allograft of claim 1.

29. The method of claim 28, wherein the wound is selected from the group consisting of an incision, a laceration, an abrasion, an avulsion, a burn, a contusion, a penetrating wound, an ulcer, a diabetic ulcer, a diabetic foot ulcer, and any combination thereof.

30. The method of claim 29, wherein the wound is a diabetic ulcer or a diabetic foot ulcer.

\* \* \* \* \*